United States Patent [19]

Stafl

[11] 4,300,570
[45] Nov. 17, 1981

[54] DIAGNOSTIC METHOD

[75] Inventor: Adolf Stafl, Brookfield, Wis.

[73] Assignee: The Medical College of Wisconsin, Inc., Milwaukee, Wis.

[21] Appl. No.: 143,429

[22] Filed: Apr. 24, 1980

[51] Int. Cl.³ ............................................. A61B 1/00
[52] U.S. Cl. ...................................... 128/665; 128/6; 354/62
[58] Field of Search ....................... 128/3, 4, 6, 18, 22, 128/23, 751, 757, 361, 665; 354/62

[56] References Cited

U.S. PATENT DOCUMENTS

| | | | |
|---|---|---|---|
| 2,280,561 | 4/1942 | Wappler | 354/62 |
| 2,746,450 | 5/1956 | Lady et al. | 128/6 |
| 3,388,645 | 6/1968 | Sullivan | 354/62 |
| 3,638,643 | 2/1972 | Hotchkiss | 128/22 X |
| 4,046,140 | 9/1977 | Born | 128/6 |

OTHER PUBLICATIONS

Bushnell, L. F., *Obstetrics & Gyn.*, vol. 22, No. 2, Aug. 1963, pp. 190-198.
Eastman Kodak Co. Cata., Dental Radiogr. & Photography, vol. 31, 1958, No. 3.
Jascalevich, M. E., *Am. J. Obstet. Gynecol.*, Nov. 1, 1971, vol. III, No. 5, pp. 692-695.

*Primary Examiner*—Kyle L. Howell
*Attorney, Agent, or Firm*—Quarles & Brady

[57] ABSTRACT

A method of detecting cancer and other abnormalities involves projecting the image of the cervix from the photograph onto a screen, viewing the screen from a short distance and noting the abnormalities.

4 Claims, 4 Drawing Figures

DIAGNOSTIC METHOD

The present invention relates to a method of detecting cervical cancer.

BACKGROUND OF THE INVENTION

Heretofore, in the early detection of cervical cancer and precancer, two methods were used: cytology and colposcopy, which is the examination of the cervix by means of an endoscope. Each method has its particular limitations and strengths in cancer detection and both methods complement each other.

Although cytology is generally recognized as the most practical and economical screening method for cervical cancer, in the last ten years, colposcopy has achieved wide recognition as a valuable tool in the clinical diagnosis of patients with abnormal cytology. Unfortunately the key for success in colposcopy is determined and limited by the expertise of the examiner. The training in colposcopy is time consuming and expensive, but without proper training it is impossible to achieve adequate results. As a result, the use of colposcopy as a screening tool has been limited by lack of suitable examiners.

A further limitation of colposcopy is that colposcopical findings are recorded in a written description of the vascular and tissue pattern of the cervix. Therefore, there is no opportunity for an objective review of the documentation of the findings. In addition, colposcopy in the hands of the inexperienced physician can result in the mis-diagnosis of a cervical lesion which can endanger the life of the patient from an invasive cancer.

Although it is generally recognized that the simultaneous use of cytology and colposcopy could effectively increase the accuracy of cervical cancer detection, nonetheless, colposcopic screening has been considered impractical and uneconomical.

In 1955, the use of stereoscopic colpophotography for cervical cancer screening was suggested. However, the use of colpophotography for screening or for evaluation of patients with abnormal cytology has proven to be difficult or even impossible for the following reasons: (1) the cost of a photocolposcope is high; (2) the depth of focus is small; (3) it is difficult technically to obtain good sharp pictures because the photography is done through the oculars of the colposcope and even a minor change or refractive error can result in a blurred picture; (4) the magnification is high, and therefore, it is necessary to prepare several pictures to cover the entire cervix; (5) the colpophotography must be done by a physician experienced in colposcopy, because he must select the proper area for colpophotography. For these reasons, colpophotography has never been used on a large scale.

SUMMARY OF THE INVENTION

It is an object of the present invention to disclose a new and inexpensive method of detecting cervical cancer and other abnormalities of the cervix.

The method of the present invention for detecting cervical cancer comprises making a single good, sharp magnified photograph of the entire cervix, projecting the image of the cervix on the photograph onto a screen and then viewing the projected image of the cervix from a short distance and noting any abnormalities.

The novel apparatus which is employed to make the photograph of the cervix includes a camera body, a telelense, an extender between the telelense and the camera body which effectively spaces the telelense a sufficient distance from the film in the camera body to provide adequate magnification, and means for illuminating the cervix for viewing and taking a photograph.

The novel apparatus of the present invention possesses the following advantages over apparatus used in the previous practice of colpophotography:
1. The apparatus is relatively inexpensive.
2. The magnification of the photograph obtained of the cervix is comparable to normal colposcopic magnification (i.e. 16X).
3. The depth of the focus of the photograph is significantly higher than with colpophotography.
4. The photograph has about the highest possible resolution.
5. The entire cervix is seen in one photograph.
6. The apparatus is portable and can be easily moved from place to place for screening.
7. The apparatus is simple to use so that non-physicians can be trained to take the photographs.

The apparatus of the present invention solves a major technical problem which is that there be at least 15 cm between the lens and the cervix and at the same time obtain high magnification of the cervix. With standard macrophotographic techniques it is possible to achieve high magnification with excellent resolution. However, with the increase in magnification there is a decrease in the distance between the object and objective. To increase the distance, a telelense (100 to 200 mm) can be used, but again the magnification is too low. In the apparatus of the present invention an extender, which is about 50 to about 100 mm long is positioned between the telelense and the camera body to provide the proper distance of object to objective, as well as the proper magnification.

The apparatus of the invention also solves the important problem of illumination of the cervix. In the preferred embodiment two separate light sources are employed. The first light source illuminates the cervix for viewing prior to taking the photograph so that the examiner can be assured that the picture is in focus. The first light source is preferably a fiber optic lamp. The second light source has to be located in the small space between the lens and the speculum through which the cervix is viewed, and it must be powerful enough to illuminate the cervix sufficiently to permit a good photograph to be taken in a short exposure time. In the preferred embodiment, the second light source is a ring strobe light positioned around the front lens of the objective of the telelense.

The method of the present invention for detecting cancer of the cervix, which I prefer to call "cervicography" and the apparatus which has been described which I call the "cervicograph" will be further described in connection with the drawings.

DESCRIPTION OF THE PREFERRED EMBODIMENT

Figure 1:
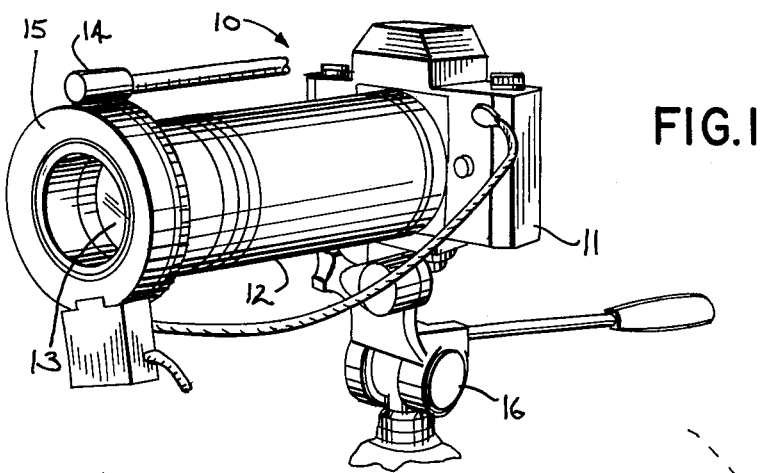
FIG. 1 is a perspective view of the apparatus of the present invention.

The preferred apparatus for taking the photograph of the cervix is shown in FIG. 1. As seen therein the cervicograph, generally referred to by the number 10, comprises a single lens reflex camera body 11, an extender 12, a telelens 13, a fiber optic light 14 and a ring strobe light 15.

The single lens reflex camera body 11 which can be held by hand or mounted on a tripod 16, as shown in the drawing, is a conventional 35 mm model which has a bayonet or screw type adapter to which an extender 12 is operatively connected. The camera body 11 includes all the required mechanisms for taking a photograph including those required to store and advance film, open and close the shutter, set exposure times and the like.

Although the extender 12 is shown in the drawing as an extender ring of fixed length, a bellows of variable length can be used in connection with a focusing rail. The length of the extender can vary from about 50 mm to about 100 mm in length. However, an extender 12 of 50 mm length is preferred for use with a 100 mm telelens 13 to obtain photographs of the entire cervix (cervicograms) having a magnification of about 16X with good resolution and depth of focus. A 200 mm telelens also can be used with appropriate adjustments in the length of the extender 12.

The fiber optic light 14 is preferably mounted as shown to camera body 11 and the frame of the ring strobe light 15. When thus positioned, the fiber optic light 14 provides a first light source which can be used to illuminate the cervix so that it can be visualized prior to taking the photograph. The ring strobe light 15 is used as a second light source to provide the more powerful light required to permit a photograph to be taken in a short exposure time. In use, both the fiber optic light 15 and the ring strobe light 15 are connected to suitable power sources (not shown).

Figure 2:
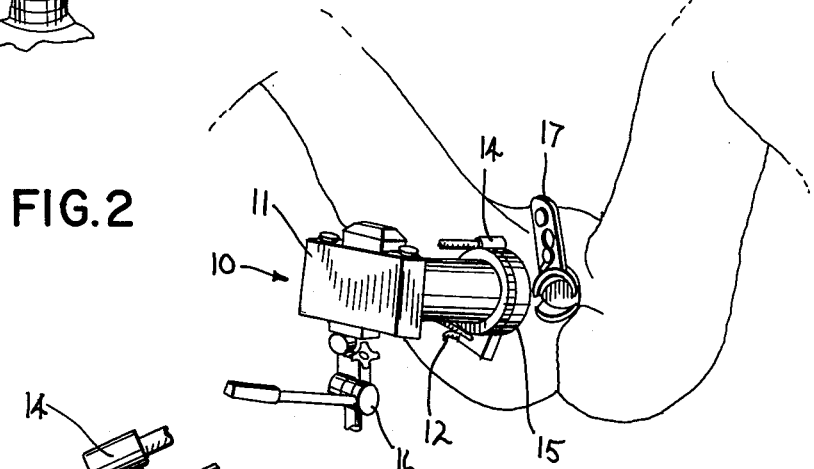
FIG. 2 is a perspective view showing the apparatus of FIG. 1 positioned for taking a photograph of the cervix.
Figure 3:
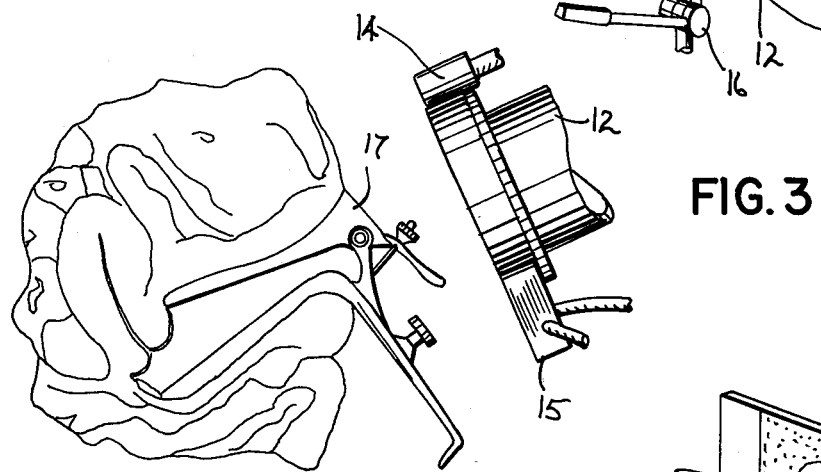
FIG. 3 is an enlarged schematic view, partly in section, of the vagina and the apparatus.
Figure 4:
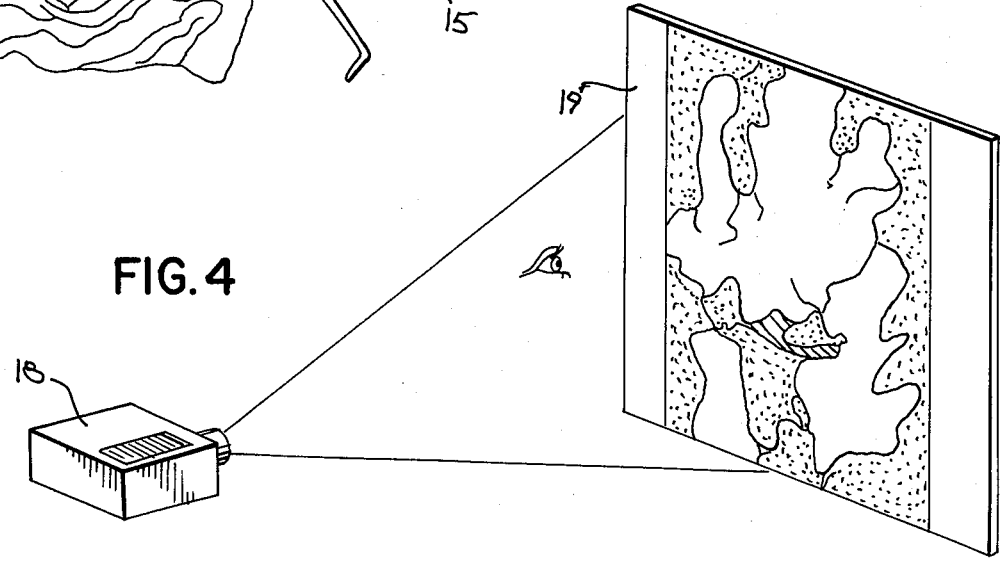
FIG. 4 is a perspective view showing the image of the cervix being projected for evaluation purposes.

The method of the present invention will now be described in connection with FIGS. 2, 3 and 4.

Prior to taking a photograph, the cervix is cleaned with dry gauze and moistened with 4% acetic acid. As seen in FIG. 2, a self-retaining speculum 17 is used to open the vagina and the cervicograph 10 is positioned as shown at least 15 cm and preferably about 19 cm from the cervix. The cervix is then illuminated using the fiber optic light 14, the camera is focused, if necessary, and a photograph is taken using the ring strobe light 15 to provide the powerful illumination required for a short exposure time. The exposure time used is preferably 1/100 sec. and the film preferably used is Ektachrome 64 slide film or a film having an equivalent ASA rating The photographic slide bearing the image of the cervix is then placed in a slide projector 18 seen only in FIG. 4, and the image projected on a screen 19 which is about 3 meters wide so that the projected image of the cervix substantially fills the screen 19. An expert evaluator (not shown) then views the projected image from a very short distance (50 cm to 1 meter) and notes his findings.

The cervicography findings are preferably classified into four groups:

(1) negative—the entire squamocolumnar junction is fully visible and no abnormal cervicography lesion is present.

(2) Suspicious—abnormal cervicography lesion (white epithelium, punctation, mosaic, atypical vessels present).

(3) Unsatisfactory—squamocolumnar junction not visible.

(4) Technically unsatisfactory—picture out of focus, under- or overexposed, or the entire cervix not visible.

In patients with suspicious cervicographic findings, the prediction of histopathological findings is recorded. Similar to colposcopy, these predictions are based on capillary pattern, intercapillary distance, color tone after acetic acid, surface pattern and the borderline between the lesion and normal epithelium. Because the magnification of the cervigraph is constant, the intercapillary distance can be measured in absolute units.

The advantages of the cervicograph and cervicography are the following:

(1) The use of the cervicograph provides permanent, objective documentation of cervical findings.
(2) The cervicograph is very portable and can be packed in a light case; therefore, cervicography screening can be done in any location.
(3) The cervicograph is simple to use. A suitable cervicogram can be obtained by a trained technician and sent to an expert for evaluation.
(4) The cost of the photographic slide or cervicogram (material and developing) is very economical. Even after consideration of the professional and technical cost, the expense of one cervicographic examination is substantially less than that for cytology.
(5) The quality control of cervicograms can be readily evaluated. Technical problems with the cervicograph can be easily recognized because the pictures will be out of focus, over- or underexposed, or the entire cervix will not be visible.
(6) The diagnostic accuracy of cervicography is similar to the diagnostic accuracy of colposcopy.
(7) The expertise of the physician evaluating the cervicograms can be measured objectively. When the physician interprets 500 to 1,000 cervicograms, a mathematical score of his expertise can be obtained. This evaluation can serve also for possible certification of cervicography experts.
(8) Permanent documentation of cervicography findings can significantly improve residency training. Special cervicography conferences can be organized with discussions about the diagnosis and the management of patients.
(9) Cervicography can be used also for research in linear studies of cervical neoplasia.

It is to be understood that, although a specific preferred apparatus has been described, the inventive method may be practiced using other apparatus to obtain an image of the cervix for evaluation purposes. For example, a single lighting means instead of the two sources of lighting might be used for illumination of the cervix. Furthermore, the picture taken need not be a slide, in which case a different type of project will be used. Therefore, it is not intended that the practice of the inventive method be limited to use of the described apparatus but only by the claims which follow:

I claim:

1. A method of detecting cervical cancer and other abnormalities of the cervix which comprises illuminating the cervix, viewing the cervix through the viewer of a single lens reflex camera equipped with an extender and a telelens which is mounted on the extender with said telelens being positioned at least 15 centimeters from the cervix, taking a slide photograph of the cervix, developing and projecting the slide photograph on a screen so that the projected image substantially fills the screen and then visually evaluating the projected image from a very close distance and noting any abnormalities.

2. The method of claim 1 in which the extender is about 50 to about 100 mms in length.

3. The method of the claim 1 in which the telelens is 100 mm.

4. A method of detecting cervical cancer and other abnormalities of the cervix which comprises illuminating the cervix and viewing the cervix through the viewer of a single lens reflex camera equipped with an extender which is about 50 to about 100 mm in length and a 100 mm telelens which is mounted on the extender and positioned at least 15 centimeters from the cervix, taking a flash slide photograph of the cervix, developing and projecting the slide photograph on a screen about three meters square so that the projected image substantially fills the screen and then visually evaluating the projected image from about 50 centimeters to about one meter from the screen and noting any abnormalities.

* * * * *